United States Patent [19]

Mochida et al.

[11] Patent Number: 4,914,099
[45] Date of Patent: Apr. 3, 1990

[54] HYDANTOIN DERIVATIVES AS ALDOSE REDUCTASE INHIBITORS

[75] Inventors: Ei Mochida, Tokyo; Kazuo Kato, Mishima; Katsuaki Kato, Gotenba; Ichitomo Miwa; Jun Okuda, both of Nagoya, all of Japan

[73] Assignee: Mochida Pharmaceutical Co., Ltd., Tokyo, Japan

[21] Appl. No.: 235,557

[22] Filed: Aug. 24, 1988

[30] Foreign Application Priority Data

Aug. 28, 1987 [JP] Japan .................. 62-214549

[51] Int. Cl.$^4$ .................. A61K 31/415; C07D 233/80
[52] U.S. Cl. .................. 514/390; 548/309; 548/311
[58] Field of Search .................. 548/311; 514/390

[56] References Cited

U.S. PATENT DOCUMENTS 3,384,643 5/1968 Sayigh et al. .................. 548/301
3,534,022 10/1970 Umemoto et al. .................. 548/311 X
4,743,611 5/1988 Malamas et al. .................. 514/390

FOREIGN PATENT DOCUMENTS 0187387 7/1986 European Pat. Off. .
0251784 1/1988 European Pat. Off. .
6097 6/1968 France .
2308626 11/1976 France .

OTHER PUBLICATIONS

*Chemical Abstracts*, vol. 95, No. 15, Oct. 12, 1981, Abstract No. 132725m.
*Chemical Abstracts*, vol. 97, No. 1, Jul. 5, 1982, Abstract No. 6774e.
*Chemical Abstracts*, vol. 99, 1983, Abstract No. 116079f.
*Chemical Abstracts*, vol. 107, 1987, Abstract No. 59037y.
*Chemical Abstracts*, vol. 109, 1988, Abstract No. 129004c.

*Primary Examiner*—Richard A. Schwartz
*Attorney, Agent, or Firm*—Oliff & Berridge

[57] ABSTRACT

The present invention relates to novel hydantoin derivatives, processes for producing said hydantoin derivatives, pharmaceutical compositions containing at least one of said hydantoin derivatives as aldose reductase inhibitors and novel intermediate compounds in the synthesis of said hydantoin derivatives.

The present invention is based on the selection of a hydantoin which is bonded by a sulfonyl group to various substituents at the 1-position of the hydantoin skeleton.

8 Claims, No Drawings

HYDANTOIN DERIVATIVES AS ALDOSE REDUCTASE INHIBITORS

BACKGROUND OF THE INVENTION

The present invention relates to novel hydantion derivatives, processes for producing hydantoin derivatives, pharmaceutical compositions containing at least one of said hydantoin derivatives as aldose reductase inhibitors and novel intermediate compounds in the synthesis of said hydantoin derivatives.

Cataract, peripheral neuropathy, retinopathy and nephropathy associated with diabetes mellitus result from abnormal accumulation of polyol metabolites converted from sugars by aldose reductase. For example, sugar cataract results from damage of lens provoked by change in osmotic pressure induced by abnormal accumulation of polyol metabolites converted from glucose or galactose by aldose reductase in lens. Consequently, it is important to inhibit aldose reductase as strongly as possible for treating and/or preventing diabetic complications mentioned above. Although several compounds have been offered as aldose reductase inhibitors, none of them is fully sufficient in inhibitory activity against the enzyme. Therefore, it has been desired to develop new compounds having a stronger inhibitory activity against aldose reductase.

SUMMARY OF THE INVENTION

An object of the present invention is to provide novel hydantoin derivatives and salts, solvates and solvates of salts thereof.

Another object of the present invention is to provide processes for producing said novel hydantoin derivatives.

A further object of the prsent invention is to provide pharmaceutical compositions comprising at least one of said novel hydantoin derivatives having an inhibitory activity against aldose reductase.

A further object of the present invention is to provide novel intermediate compounds in the synthesis of said novel hydantoin derivatives.

The present inventors previously found that substituted phenylsulfonylhydantoin derivatives and naphthalenylsulfonylhydantoin derivatives had a strong inhibitory activity against aldose reductase and accomplished an invention on aldose reductase inhibitors. (JP-A-56 213,518, 60 207,113, 61 43770)

Furthermore, the present inventors have made extensive researches on a series of compounds having an inhibitory activity against aldose reductase and found novel hydantoin derivatives having an extremely strong inhibitory activity against aldose reductase. They are extremely useful for the treatment and/or prevention of various forms of diabetic complications based on the accumulation of polyol metabolites.

DETAILED DESCRIPTION OF THE INVENTION

As a result of extensive investigations concerning development of hydantoin derivatives having a satisfactory inhibitory activity against aldose reductase, the present inventors have found that novel hydantoin derivatives represented by the general formula (I) satisfy this requirement and have accomplished the present invention.

The present invention is based on the selection of a hydantoin which is bonded by a sulfonyl group to various substituents at the 1-position of the hydantoin skeleton.

The present invention is directed to novel hydantoin derivatives represented by the general formula (I):

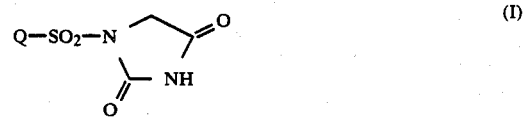

and non-toxic salts, solvates and solvates of non-toxic salts thereof; wherein Q represents an alkyl group having 1 to 8 carbon atoms, a cycloalkyl group having 3 to 6 carbon atoms, a biphenylyl group, a monocyclic or a fused heterocyclic group which may be substituted or a group:

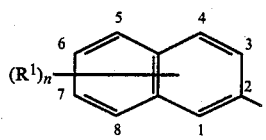

wherein $R^1$ represents an amino group which may be substituted with lower alkyl groups and/or acyl groups, a halogen atom, a lower alkyl group, an alkoxy group, a nitro group or a cyano group, or combination of any of these groups when n represents an integer of 2 or more, and n represents an integer of 1, 2, 3 or 4. In the naphthalene depicted above, numerals show positions on the naphthalene as referred to herein.

The present invention is also directed to the process for preparing above-mentioned hydantoin derivatives.

The present invention is further directed to pharmaceutical compositions characterized by containing at least one of these hydantoin derivatives as active component(s).

The present invention is further directed to novel intermediate compounds in the synthesis of above-mentioned hydantoin derivatives.

In the hydantoin derivatives of the present invention represented by the general formula (I), it is known that the hydantoin moiety exhibits tautomerism as shown below:

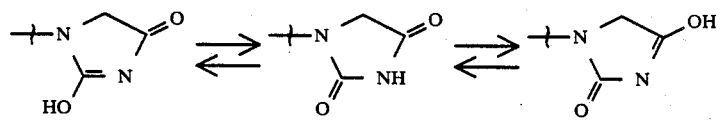

Since these tautomeric isomers are generally deemed to be the same substance, the compounds of the present invention represented by the general formula (I) also include all of these tautomeric isomers.

The compounds represented by the general formula (I) may form salts with base. Typical examples of salts with base of the compounds represented by the general formula (I) include pharmaceutically acceptable salts such as alkali metal salts (such as sodium salts, potassium salts, etc.), alkaline earth metal salts (such as calcium salts, etc.), salts with organic bases (such as ammonium salts, benzylamine salts, diethylamine salts, etc.) or salts of amino acids (such as arginine salts, lysine salts, etc.). These salts of the compounds represented by the general formula (I) may be mono-salts or di-salts which may be salts of the hydantoin moiety and/or salts of the carboxy group contained in the Q group.

The compounds represented by the general formula (I) may also form acid addition salts. Typical example of acid addition salts of the compounds represented by the general formula (I) include pharmaceutically acceptable salts, such as salts of inorganic acids (such as hydrochlorides, hydrobromides, sulfates, phosphates, etc.), salts of organic acids (such as acetates, citrates, maleates, tartrates, benzoates, ascorbate, ethanesulfonates, toluenesulfonates, etc.) or salts of amino acids (such as aspartates, glutamates, etc.). These salts of the compounds represented by the general formula (I) may be salts of the heterocyclic moiety in the Q group.

In the compounds of the present invention represented by the general formula (I), the lower alkyl group can be defined more specifically as a straight or branched lower alkyl group having 1 to 4 carbon atoms such as methyl, ethyl, isopropyl, tert-butyl, etc. The alkoxy group can be defined more specifically as a straight or branched lower alkoxy group having 1 to 4 carbon atoms such as methoxy, ethoxy, isopropoxy, tert-butoxy, etc. The acyl group can be defined more specifically as a straight or branched lower acyl group having 1 to 5 carbon atoms such as formyl, acetyl, propanoyl, butanoyl, pivaloyl, etc.

In the compounds of the present invention represented by the general formula (I), the heterocyclic group can be defined as a monocyclic heterocyclic group such as pyrrolyl, pyrrolinyl, imidazolyl, pyrazolyl, triazolyl, tetrazolyl, oxazolyl, isoxazolyl, oxadiazolyl, thiazolyl, isothiazolyl, thiazolinyl, thiadiazolyl, thiatriazolyl, thienyl, furyl, pyrrolidinyl, imidazolidinyl, thiazolidinyl, pyridyl or its N-oxide, pyrazinyl, pyrimidinyl, pyridazinyl, piperidyl, piperazinyl, morpholinyl, triazinyl, etc., or a fused heterocyclic group such as indolyl, isoindolyl, benzimidazolyl, quinolyl, isoquinolyl, quinazolinyl, cinnolinyl, phthalazinyl, quinoxalinyl, indazolyl, benzotriazolyl, benzoxazolyl, benzoxadiazolyl, benzothiazolyl, benzothiadiazolyl, benzisoxazolyl, benzisothiazolyl, benzothiophenyl (benzo[b]thiophenyl or benzo[c]thiophenyl), benzofuranyl (benzo[b]furanyl or isobenzofuranyl), chromenyl, chromanyl, coumarinyl, chromonyl, triazolopyridyl, tetrazolopyridyl, purinyl, thiazolopyrimidinyl, triazolopyrimidinyl, thiadiazolopyrimidinyl, thiazolopyridazinyl, naphthyridinyl, xanthenyl, phenoxathiinyl, phenoxazinyl, phenothiazinyl, carbazolyl, etc. The above-mentioned heterocyclic groups may be substituted with a group such as a lower alkyl group (such as methyl, ethyl, isopropyl, tert-butyl, etc.), an acyl group (such as formyl, acetyl, propanoyl, butanoyl, pivaloyl, etc.), an alkoxy group (such as methoxy, ethoxy, isopropoxy, tert-butoxy, etc.), an aryl group, a cyano group, a carboxy group, a nitro group or a halogen atom (such as fluoro, chloro, bromo, etc.), or combination of any of these groups.

The compounds of the present invention represented by the general formula (I) can be produced by the processes described as follows. Namely;

The sulfonyl halide derivative represented by the general formula (II):

$$Q-SO_2-Y \qquad (II)$$

wherein Q has the same significance as defined above and Y represents a halogen atom, is reacted with a glycine derivative represented by the general formula (III):

$$NH_2CH_2CO-R^2 \qquad (III)$$

wherein $R^2$ represents a hydroxy group, an alkoxy group or an amino group which may be substituted with an alkoxycarbonyl group, to give the corresponding sulfonylglycine derivative represented by the general formula (IV):

$$Q-SO_2NHCH_2CO-R^2 \qquad (IV)$$

wherein Q and $R^2$ have the same significance as defined above. The condensation reaction is carried out generally in an aqueous solution, in an organic solvent (such as dichloromethane, chloroform, dioxane, tetrahydrofuran, acetonitrile, ethyl acetate, acetone, N,N-dimethylformamide, etc.) or in a mixed solvent of an aqueous solution and an organic solvent, preferably in the presence of deacidifying agent. As the deacidifying agent, triethylamine, diethylaniline, pyridine, etc. is employed in the organic solvent system, and in the aqueous system, aqueous alkali (such as sodium carbonate, sodium bicarbonate, potassium carbonate, sodium hydroxide, etc.) is employed. The condensation reaction is carried out at temperatures ranging from about −20° to 80° C., preferably 0° C. to room temperature.

When $R^2$ represents an amino group in the general formula (IV), the sulfonylglycine derivative is represented by the general formula (IV'):

$$Q-SO_2NHCH_2CONH_2 \qquad (IV')$$

wherein Q has the same significance as defined above.

The sulfonylglycine derivative represented by the general formula (IV') is cyclized using a haloformic acid ester (such as methyl chloroformate, ethyl chloroformate, etc.) in the presence of a base (such as sodium hydride, potassium hydride, butyl lithium, etc.) to give the corresponding hydantoin derivative of the present invention represented by the general formula (I). The cyclization reaction is carried out generally in an inert solvent (such as N,N-dimethylformamide, dimethylsulfoxide, ethyl ether, tetrahydrofuran, dioxane, dichloromethane, etc.) and at temperatures ranging from about −20° to 120° C., preferably 0° to 80° C.

When $R^2$ represents a hydroxy group or an alkoxy group in the general formula (IV), the sulfonylglycine derivative is represented by the general formula (IV")

$$Q-SO_2NHCH_2CO-R^{2'} \qquad (IV'')$$

wherein Q has the same significance as defined above and $R^{2'}$ represents a hydroxy group or an alkoxy group.

The sulfonylglycine derivative represented by the general formula (IV") is cyclized with a thiocyanate derivative (such as ammonium thiocyanate, potassium thiocyanate, etc.) in the presence of an acid anhydride (such as acetic anhydride, propionic anhydride, etc.) and, if necessary and desired, a base (such as pyridine, triethylamine, etc.) to give the corresponding 2-thiohydantoin derivative. If necessary and desired, the cyclization reaction is carried out after hydrolysis of ester than $R^2$ represents an alkoxy group. The cyclization reaction is carried out generally in an inert solvent (such as pyridine, triethylamine, N,N-dimethylformamide, dimethylsulfoxide, etc.) and at temperatures ranging from 0° to 120° C., preferably room temperature to 100° C. Further, the 2-thiohydantoin derivative obtained by said cyclization is oxidized using oxidizing agent (such as nitric acid, chlorine, iodine chloride, potassium permanganate, hydrogen peroxide, dimethylsulfoxide-sulfuric acid, etc.) to give the corresponding hydantoin derivatives of the present invention represented by the general formula (I).

To demonstrate the utility of the compounds of the present invention, experimental examples of representative compounds are shown below.

Compounds in the present invention
Compound 1: 1-(1-chloronaphthalen-2-ylsulfonyl)hydantoin
Compound 2: 1-(3-chloronaphthalen-2-ylsulfonyl)hydantoin
Compound 3: 1-(5-chloronaphthalen-2-ylsulfonyl)hydantoin
Compound 4: 1-(6-chloronaphthalen-2-ylsulfonyl)hydantoin
Compound 5: 1-(7-chloronaphthalen-2-ylsulfonyl)hydantoin
Compound 6: 1-(8-chloronaphthalen-2-ylsulfonyl)hydantoin
Compound 7: 1-(3,6-dichloronaphthalen-2-ylsulfonyl)hydantoin
Compound 8: 1-(1-bromonaphthalen-2-ylsulfonyl)hydantoin
Compound 9: 1-(3-bromonaphthalen-2-ylsulfonyl)hydantoin
Compound 10: 1-(6-bromonaphthalen-2-ylsulfonyl)hydantoin
Compound 11: 1-(5-nitronaphthalen-2-ylsulfonyl)hydantoin
Compound 12: 1-(3-methylnaphthalen-2-ylsulfonyl)hydantoin
Compound 13: 1-(6-methyl-5-nitronaphthalen-2-ylsulfonyl)hydantoin
Compound 14: 1-(7-methylnaphthalen-2-ylsulfonyl)hydantoin
Compound 15: 1-(6-methoxy-5-nitronaphthalen-2-ylsulfonyl)hydantoin
Compound 16: 1-(benzo[b]thiophen-2-ylsulfonyl)hydantoin
Compound 17: 1-(3-chlorobenzo[b]thiophen-2-ylsulfonyl)hydantoin
Compound 18: 1-(5-chlorobenzo[b]thiophen-2-ylsulfonyl)hydantoin
Compound 19: 1-(benzo[b]furan-2-ylsulfonyl)hydantoin
Compound 20: 1-(5-chlorobenzo[b]furan-2-ylsulfonyl)hydantoin
Compound 21: 1-(5-bromobenzo[b]furan-2-ylsulfonyl)hydantoin
Compound 22: 1-(benzothiazol-2-ylsulfonyl)hydantoin
Compound 23: 1-(coumarin-6-ylsulfonyl)hydantoin
Compound 24: 1-(2,5-dichlorothiophen-3-ylsulfonyl)hydantoin Reference compounds
Compound 25: 1-(naphthalen-2-ylsulfonyl)hydantoin
Compound 26: sorbinil

EXPERIMENTAL EXAMPLE 1

The inhibitory activities of hydantoin derivatives on rat lens aldose reductase were measured according to the procedure of Inagaki et al. (K. Inagaki et al., Arch. Biochem. Biophys., 216, 337 (1982)) with slight modifications. Assays were performed in 0.1M phosphate buffer (pH 6.2) containing 0.4M ammonium sulfate, 10 mM DL-glyceraldehyde, 0.16 mM NADPH and aldose reductase (0.010–0.016 units) in a total volume of 1.0 ml. To this mixture was added 10 μl of the solution of each hydantoin derivative to be tested, and the decrease in absorbance at 340 nm was measured with a spectrophotometer.

The concentrations of typical hydantoin derivatives of the present invention required to produce 50% inhibition are shown in table 1.

TABLE 1

| Compounds | $IC_{50}$ (μmol/l) |
|---|---|
| 1 | 0.29 |
| 2 | 0.16 |
| 3 | 0.19 |
| 4 | 0.14 |
| 5 | 0.39 |
| 6 | 0.46 |
| 7 | 0.24 |
| 8 | 0.094 |
| 9 | 0.35 |
| 10 | 0.17 |
| 11 | 0.10 |
| 12 | 0.14 |
| 13 | 0.027 |
| 14 | 0.35 |
| 15 | 0.038 |
| 25 | 0.66 |

Compounds 1 to 15 of the present invention showed stronger inhibitory activities against aldose reductase than reference compound 25 did. Above all, compound 13 and 15 were ten times or more potent than reference compound 25.

EXPERIMENTAL EXAMPLE 2

The inhibitory activities of hydantoin derivatives on bovine lens aldose reductase were measured according to the procedure of Inagaki et al. (K. Inagaki et al., Arch. Biochem. Biophys., 216, 337 (1982)) with slight modifications. Assay procedure was the same as described in Experimental example 1 except that bovine lens aldose reductase preparation was used instead of rat lens aldose reductase preparation.

The concentrations of the typical hydantoin derivatives of the present invention required to produce 50% inhibition are shown in table 2.

TABLE 2

| Compounds | $IC_{50}$ (μmol/l) |
|---|---|
| 13 | 0.10 |
| 15 | 0.23 |
| 16 | 0.39 |
| 17 | 0.12 |
| 18 | 0.24 |
| 20 | 0.36 |
| 21 | 0.30 |
| 22 | 0.34 |
| 23 | 0.22 |
| 24 | 0.29 |
| 26 | 0.65 |

Compounds 13, 15, 16, 17, 18, 20, 21, 22, 23 and 24 of the present invention showed stronger inhibitory activities against aldose reductase than reference compound 26 did, which is a well known potent aldose reductase inhibitor. Compound 17, 18, 23 and 24 were as potent as compound 13 and 15, which showed strongest inhibitory activities in experimental example 1.

EXPERIMENTAL EXAMPLE 3

Hydantoin derivatives of the present invention were examined for acute toxicity. Groups of 5 ICR strain mice were orally administered with compound 7, 13, 14, 15, 16, 17, 19 or 24 of the present invention in a dose of 1 g/kg, and no change was observed in any of the eight groups over the one-week period after the administration.

Since the compounds of the present invention have strong inhibitory activities against aldose reductase and lower toxicity, pharmaceutical compositions containing at least one of these compounds as active component(s) are useful for the treatment and/or prevention of diabetic complications based on the accumlation of polyol metabolites.

The hydantoin derivatives provided by the present invention can be employed as pharmaceutical compositions, for example, in the form of pharmaceutical compositions containing hydantoin derivatives together with appropriate pharmaceutically acceptable carrier or medium such as sterilized water, edible oils, and non-toxic organic solvents. They may be mixed with excipients, binders, lubricants, coloring agents, corrigents, emulsifying agents or suspending agents to prepare tablets, powders, syrups, injections, eye drops, suppositories, ointments or inhalants. These agents can be administered either orally or parenterally and the amount of administration may be in the range of 1 to 3000 mg/day and may also be adjusted according to the patient conditions.

Hereafter the present invention will be described with references to the examples below but is not deemed to be limited thereof.

EXAMPLE 1

Preparation of 1-(1-chloronaphthalen-2-ylsulfonyl)hydantoin (compound 1).

Step 1

Preparation of N-(1-chloronaphthalen-2-ylsulfonyl)glycine.

To a solution of potassium carbonate (21 g) and glycine (11 g) in water (300 ml) was added 1-chloronaphthalen-2-ylsulfonyl chloride (31 g) at room temperature, and the mixture was stirred under reflux for 30 minutes. After cooling to room temperature, the resultant solution was acidified with 2N hydrochloric acid to a pH in the range of 1 to 2, and the formed precipitate was separated by filtration to give 33 g of the objective compound.

Melting point: 185.5°–200.7° C.
IR (KBr, cm$^{-1}$):3380, 1720, 1325, 1135
NMR (DMSO-d$_6$, ppm): 3.63 (2H, s), 7.59–8.51 (7H, m)

Step 2

Preparation of 1-(1-chloronaphthalen-2-ylsulfonyl)-2-thiohydantoin.

Anhydrous pyridine (19 ml), ammonium thocyanate (17 g) and acetic anhydride (50 ml) were added to the product obtained in Step 1 (30 g), and the mixture was heated with stirring on a boiling water bath for 15 minutes. After cooling to room temperature, the resultant solution was poured into ice-water (300 ml), and the formed precipitate was separated by filtration to give 30.6 g of the objective compound.

Melting point: 268.6° C. (decomposition)
IR (KBr, cm$^{-1}$): 3150, 1790, 1765, 1380, 1190
NMR (DMSO-d$_6$, ppm): 4.93 (2H, s), 7.66–8.53 (5H, m), 8.78 (1H, s)

Step 3

Preparation of 1-(1-chloronaphthalen-2-ylsulfonyl)hydantoin.

A mixture of the product obtained in Step 2 (20 g) and 50% (w/v) nitric acid (100 ml) was heated with stirring on a boiling water bath for 40 minutes, and the resultant solution was cooled in an ice bath. The formed precipitate was separated by filtration and washed successively with water, ethyl alcohol, methyl alcohol and dichloromethane to give 4.8 g of the objective compound.

Melting point: 258.3°–260.5° C.
IR (KBr, cm$^{-1}$): 3140, 1740, 1370, 1180
NMR (DMSO-d$_6$, ppm): 4.74 (2H, s), 7.80–8.39 (6H, m), 11.77 (1H, s)

EXAMPLE 2

Preparation of 1-(1-bromonaphthalen-2-ylsulfonyl)hydantoin (compound 8).

Step 1

Preparation of N-(1-bromonaphthalen-2-ylsulfonyl)glycine.

Starting from 1-bromonaphthalen-2-ylsulfonyl chloride, the objective compound was obtained in a manner similar to Step 1 of Example 1.

Melting point: 199.7°–204.1° C.
NMR (DMSO-d$_6$, ppm): 3.77 (2H, d, J=6.0 Hz), 7.49–8.47 (7H, m)

Step 2

Preparation of 1-(1-bromonaphthalen-2-ylsulfonyl)-2-thiohydantoin.

Starting from the product obtained in Step 1, the objective compound was obtained in a manner similar to Step 2 of Example 1.

Melting point: 253.7° C. (decomposition)
NMR (DMSO-d$_6$, ppm): 5.01 (2H, s), 7.71–8.80 (6H, m)

Step 3

Preparation of 1-(1-bromonaphthalen-2-ylsulfonyl)hydantoin.

A mixture of the product obtained in Step 2 (7.5 g) and 50% (w/v) nitric acid (50 ml) was heated with stirring on a boiling water bath for 30 minutes and 60% (w/v) nitric acid (25 ml) was added. The reaction mixture was heated with stirring on a boiling water bath for 2 hours. The resultant solution was cooled in an ice bath, and the formed precipitate was separated by filtration and washed successively with water, methyl alcohol and dichloromethane to give 2.7 g of the objective compound.

Melting point: 287.4°–292.5° C.
IR (KBr, cm$^{-1}$): 3200, 1740, 1370, 1180
NMR (DMSO-d$_6$, ppm): 4.78 (2H, s), 7.79–8.52 (6H, m), 11.75 (1H, s)

EXAMPLE 3

Preparation of
1-(3,6-dichloronaphthalen-2-ylsulfonyl)hydantoin
(compound 7).

Step 1

Preparation of N-(3,6-dichloronaphthalen-2-ylsulfonyl)glycine.

To a solution of potassium carbonate (11.7 g) and glycine (6.4 g) in water (140 ml) were added 3,6-dichloronaphthalen-2-ylsulfonyl chloride (20.8 g) and dioxane (50 ml) at room temperature, and the mixture was stirred under reflux for 2 hours. After cooling to room temperature, the resultant solution was acidified with 2N hydrochloric acid to a pH in the range of 1 to 2, and extracted with ethyl acetate. The organic layer was washed with water, then with saturated aqueous NaCl solution, and dried over anhydrous sodium sulfate. Ethyl acetate was removed in vacuo to give 19.0 g of the objective compound.

Melting point: 185.0°–188.2° C.

NMR (DMSO-$d_6$, ppm): 3.82 (2H, d, J=8.0 Hz), 7.49–8.34 (5H, m), 8.63 (1H, s)

Step 2

Preparation of 1-(3,6-dichloronaphthalen-2-ylsulfonyl)-2-thiohydantoin

Starting from the product obtained in Step 1, the objective compound was obtained in a manner similar to Step 2 of Example 1.

Melting point: 252.8° C. (decomposition)

NMR (DMSO-$d_6$, ppm): 4.92 (2H, s), 7.38–8.32 (4H, m), 8.90 (1H, s)

Step 3

Preparation of 1-(3,6-dichloronaphthalen-2-ylsulfonyl)hydantoin.

Starting from the product obtained in Step 2, the objective compound was obtained in a manner similar to Step 3 of Example 1.

Melting point: 263.1°–266.5° C.

IR (KBr, cm$^{-1}$): 3220, 1740, 1355, 1170

NMR (DMSO-$d_6$, ppm): 4.67 (2H, s), 7.74 (1H, d), 8.18–8.43 (3H, m), 8.98 (1H, s), 11.77 (1H, bs)

EXAMPLE 4

Preparation of
1-(5-nitronaphthalen-2-ylsulfonyl)hydantoin
(compound 11).

Step 1

Preparation of N-(5-nitronaphthalen-2-ylsulfonyl)glycine.

To a solution of potassium carbonate (3.2 g) and glycine (1.7 g) in water (50 ml) was added 5-nitronaphthalen-2-ylsulfonyl chloride (5 g) at room temperature, and the mixture was stirred under reflux for 5 minutes. After cooling to room temperature, the resultant solution was acidified with 2N hydrochloric acid to a pH in the range of 1 to 2, and the formed precipitate was separated by filtration to give 5.4 g of the objective compound.

Melting point: 235.7°–240.7° C.

IR (KBr, cm$^{-1}$): 3353, 1718, 1519, 1335, 1143

NMR (DMSO-$d_6$, ppm): 3.70 (2H, d, J=5.9 Hz), 7.73–8.64 (7H, m), 12.60 (1H, bs)

Step 2

Preparation of 1-(5-nitronaphthalen-2-ylsulfonyl)-2-thiohydantoin.

Starting from the product obtained in Step 1, the objective compound was obtained in a manner similar to Step 2 of Example 1.

Melting point: 249.6°–254.8° C.

IR (KBr, cm$^{-1}$): 3303, 1794, 1767, 1519, 1453, 1343, 1163

NMR (DMSO-$d_6$, ppm): 4.88 (2H, s), 7.80–9.03 (6H, m), 12.67 (1H, bs)

Step 3

Preparation of 1-(5-nitronaphthalen-2-ylsulfonyl)hydantoin.

Starting from the product obtained in Step 2, the objective compound was obtained in a manner similar to Step 3 of Example 1.

Melting point: 241.6°–245.6° C.

IR (KBr, cm$^{-1}$): 3265, 1801, 1737, 1523, 1340 1170

NMR (DMSO-$d_6$, ppm): 4.58 (2H, s), 7.81–8.96 (6H, m), 11.64 (1H, bs)

EXAMPLE 5

Preparation of
1-(6-acetamidonaphthalen-2-ylsulfonyl)hydantoin.

Step 1

Preparation of N-(6-acetamidonaphthalen-2-ylsulfonyl)glycine.

Starting from 6-acetamidonaphthalen-2-ylsulfonyl chloride, the objective compound was obtained in a manner similar to Step 1 of Example 1.

Melting point: 202.2°–204.0° C.

NMR (DMSO-$d_6$, ppm): 2.11 (3H, s), 3.36 (2H, s), 5.01 (1H, bs), 7.58–8.40 (7H, m), 10.38 (1H, bs)

Step 2

Preparation of 1-(6-acetamidonaphthalen-2-ylsulfonyl)-2-thiohydantoin.

Starting from the product obtained in Step 1, the objective compound was obtained in a manner similar to Step 2 of Example 1.

Melting point: 274.0°–276.9° C.

NMR (DMSO-$d_6$, ppm): 2.13 (3H, s), 4.85 (2H, s), 7.74–8.65 (6H, m), 10.30 (1H, s), 12.60 (1H, bs)

Step 3

Preparation of 1-(6-acetamidonaphthalen-2-ylsulfonyl)hydantoin.

To a mixture of the product obtained in Step 2 (1.45 g), sodium bicarbonate (16 g), carbon tetrachloride (40 ml) and water (120 ml) was added slowly a solution of iodine monochloride (6.9 ml) in 1N hydrochloric acid (40 ml) at room temperature. After stirring at room temperature for 10 minutes, 6N hydrochloric acid (320 ml) was added, and the resultant solution was extracted with ethyl acetate. The organic layer was washed with saturated aqueous sodium sulfite solution, then with saturated aqueous NaCl solution, and dried over anhydrous sodium sulfate. Ethyl acetate was removed in vacuo, and the residue was washed with dichloromethane to give 1.0 g of the objective compound.

Melting point: >300° C.

IR (KBr, cm$^{-1}$): 3400, 3250, 1740, 1360, 1165

NMR (DMSO-d₆, ppm): 2.14 (3H, s), 4.55 (2H, s), 7.60–8.56 (6H, m), 10.49 (1H, s), 11.60 (1H, s)
Compounds of Example 6 to 25 prepared in a manner similar to Example 1 are summarized in the following table 3 together with corresponding IR and NMR data and melting points.
TABLE 3
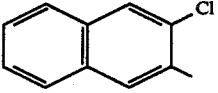
| Ex. No. | Q | IR(KBr,cm⁻¹) | NMR(DMSO-d₆,ppm) | M.P. (°C.) |
|---|---|---|---|---|
| 6 | 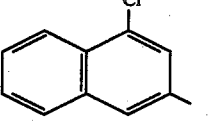 | 3250,1735, 1350,1160 | 4.57(2H,s), 7.67~8.34(5H,m), 8.74(1H,s), 11.60(1H,bs) | 259.6~ 262.0 |
| 7 | 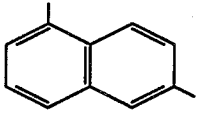 | 3250,1735, 1350,1165 | 4.58(2H,s), 7.89~8.73(6H,m), 11.62(1H,bs) | 256.7~ 261.0 |
| 8 | 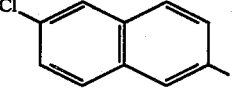 | 3230,1730, 1350,1160 | 4.57(2H,s), 7.62~8.80(6H,m), 11.62(1H,bs) | 293.0~ 299.5 |
| 9 | 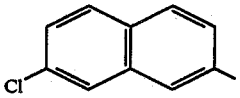 | 3230,1720, 1350,1150 | 4.57(2H,s), 7.69~8.75(6H,m), 11.61(1H,bs) | 238.7~ 241.4 |
| 10 | 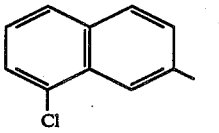 | 3160,1730, 1375,1170 | 4.56(2H,s), 7.71~8.70(6H,m), 11.62(1H,bs) | 261.0~ 263.9 |
| 11 | 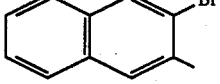 | 3230,1730, 1350,1160 | 4.56(2H,s), 7.69~8.82(6H,m), 11.61(1H,bs) | 233.7~ 235.3 |
| 12 | 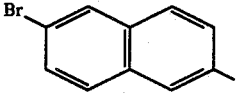 | 3240,1730, 1360,1180 | 4.72(2H,s), 7.74~8.26(4H,m), 8.54(1H,s), 8.96(1H,s), 11.77(1H,bs) | 298.0~ 303.0 |
| 13 | 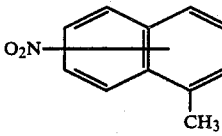 | 3220,1730, 1350,1160 | 4.57(2H,s), 7.80~8.74(6H,m), 11.61(1H,bs) | 255.6~ 258.6 |
| 14 | 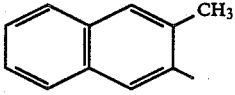 | 3250,1735, 1520,1340, 1150 | 3.08(3H,s), 4.58(2H,s), 7.90~8.73(5H,m), 11.69(1H,bs) | 232.0~ 236.5 |
| 15 |  | 3200,1725, 1340,1160 | 2.70(3H,s), 4.55(2H,s), 7.62~8.14(5H,m), 8.75(1H,s), 11.65(1H,bs) | 271.4~ 277.3 |

TABLE 3-continued
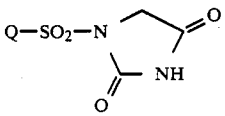
| Ex. No. | Q | IR(KBr,cm$^{-1}$) | NMR(DMSO-d$_6$,ppm) | M.P. (°C.) |
|---|---|---|---|---|
| 16 | 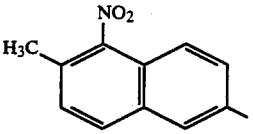 | 3170,1730, 1530,1370, 1170 | 2.52(3H,s), 4.55(2H,s), 7.74~8.48(4H,m), 8.85(1H,s), 11.62(1H,bs) | 295.0~ 296.1 |
| 17 | 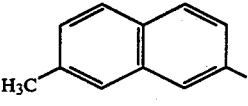 | 3240,1735, 1350,1160 | 2.53(3H,s), 4.56(2H,s), 7.51~8.63(6H,m), 11.58(1H,bs) | 212.1~ 215.3 |
| 18 | 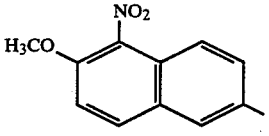 | 3180,1740, 1530,1370, 1170 | 4.11(3H,s), 4.54(2H,s), 7.75~8.83(5H,m), 11.61(1H,bs) | 285.9~ 286.4 |
| 19 | 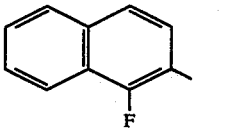 | 3170,1720, 1365,1180 | 4.56(2H,s), 7.78~8.20(6H,m), 11.67(1H,bs) | 231.0~ 234.0 |
| 20 | 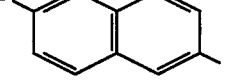 | 3230,1730, 1350,1150 | 4.50(2H,s), 7.78~8.39(6H,m), 11.60(1H,bs) | 162.6~ 166.0 |
| 21 | 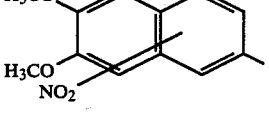 | 3250,1735, 1365,1165 | 4.02(3H,s), 4.06(3H,s), 4.54(2H,s), 7.72~8.80(4H,m), 11.65(1H,bs) | 228.0~ 230.0 |
| 22 | 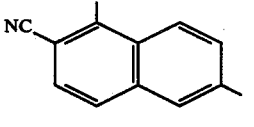 | 3150,2230, 1735,1380, 1170 | 4.57(2H,s), 8.01~8.91(5H,m), 11.65(1H,bs) | 279.0~ 285.0 |
| 23 | 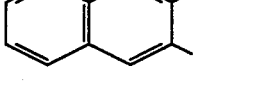 | 3230,2240, 1740,1380, 1160 | 4.58(2H,s), 7.93~8.49(4H,m), 8.75(1H,s), 8.84(1H,s), 11.63(1H,bs) | 261.6~ 264.6 |
| 24 | 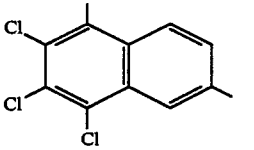 | 3230,1740, 1380,1170 | 4.54(2H,s), 8.27~8.87(3H,m), 11.60(1H,bs) | >300 |
| 25 | 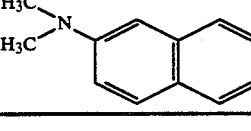 | 3240,1740, 1370,1170 | 2.94(6H,s), 4.53(2H,s), 7.35~8.59(6H,m), 11.56(1H,bs) | 102.9~ 104.5 |

EXAMPLE 26

Preparation of 1-(benzo[b]thiophen-2-ylsulfonyl)hydantoin (compound 16).

Step 1

Preparation of N-(benzo[b]thiophen-2-ylsulfonyl)glycine.

Starting from benzo[b]thiophen-2-ylsulfonyl chloride, the objective compound was obtained in a manner similar to Step 1 of Example 1.

Melting point: 171.3°-172.4° C.
IR (KBr, cm$^{-1}$): 3267, 1735, 1352, 1258, 1115, 1115
NMR (DMSO-d$_6$, ppm): 3.73 (2H, d, J=6.0 Hz), 7.39-7.61 (2H, m), 7.77-8.13 (3H, m), 8.51 (1H, d, J=6.0 Hz), 12.68 (1H, bs)

Step 2

Preparation of 1-(benzo[b]thiophen-2-ylsulfonyl)-2-thiohydantoin.

Starting from the product obtained in Step 1, the objective compound was obtained in a manner similar to Step 2 of Example 1.

Melting point: 218.6° C. (decomposition)
IR (KBr, cm$^{-1}$): 1759, 1374, 1255, 1171, 1157
NMR (DMSO-d$_6$, ppm): 4.74 (2H, s), 7.35-7.69 (2H, m), 8.04-8.21 (2H, m), 8.45 (1H, s), 12.72 (1H, bs)

Step 3

Preparation of 1-(benzo[b]thiophen-2-ylsulfonyl)hydantoin.

To a suspension of iodine monochloride (7.12 ml) in 1N hydrochloric acid (200 ml) were added successively the product obtained in Step 2 (8.50 g) and dichloromethane (200 ml). The mixture was stirred for 20 minutes at room temperature. After adding sodium bicarbonate (6.85 g), the reaction mixture was stirred for 15 minutes and extracted twice with ethyl acetate (1l+300 ml). The organic layer was washed with saturated aqueous sodium bisulfite solution and then saturated aqueous NaCl solution, and dried over anhydrous magnesium sulfate. Ethyl acetate was removed in vacuo, the residue was washed with dichloromethane to give 4.83 g of the objective compound.

Melting point: 251.8°-254.2° C.
IR (KBr, cm$^{-1}$): 3245, 1803, 1740, 1376, 1352, 1167
NMR (DMSO-d$_6$, ppm): 4.48 (2H, s), 7.51-7.63 (2H, m), 8.05-8.20 (2H, m), 8.33 (1H, s), 11.71 (1H, bs)

EXAMPLE 27

Preparation of 1-(benzo[b]furan-2-ylsulfonyl)hydantoin (compound 19).

Step 1

Preparation of N-(benzo[b]furan-2-ylsulfonyl)glycine.

Starting from benzo[b]furan-2-ylsulfonyl chloride, the objective compound was obtained in a manner similar to Step 1 of Example 1.

Melting point: 177.0°-178.2° C.
IR (KBr, cm$^{-1}$): 3289, 1724, 1347, 1162
NMR (DMSO-d$_6$, ppm): 3.77 (2H, d, J=6.3 Hz), 7.35-7.81 (5H, m), 8.72 (1H, t, J=6.3 Hz), 12.69 (1H, bs)

Step 2

Preparation of 1-(benzo[b]furan-2-ylsulfonyl)-2-thiohydantoin.

To a suspension of the product obtained in Step 1 (37.0 g) and ammonium thiocyanate (24.3 g) in acetic anhydride (100 ml) was added dropwise anhydrous pyridine (30.5 ml), and the mixture was heated with stirring for 1.5 hours at 70°-80° C. After cooling to room temperature, the resultant solution was poured into ice (800 g), and the formed precipitate was separated by decantation. The precipitate was washed with water and dried to give 18.5 g of the objective compound.

Melting point: 213.0° C. (decomposition)
IR (KBr, cm$^{-1}$): 3080, 1759, 1386, 1255, 1167 1086
NMR (DMSO-d$_6$, ppm): 4.76 (2H, s), 7.34-8.04 (5H, m), 12.81 (1H, bs)

Step 3

Preparation of 1-(benzo[b]furan-2-ylsulfonyl)hydantoin.

Starting from the product obtained in Step 2, the objective compound was obtained in a manner similar to Step 3 of Example 26.

Melting point: 255.9°-256.4° C.
IR (KBr, cm$^{-1}$): 1803, 1735, 1398, 1360, 1166
NMR (DMSO-d$_6$, ppm): 4.49 (2H, s), 7.33-8.08 (5H, m), 11.79 (1H, bs)

Compounds of Example 28 to 52 prepared in a manner similar to Example 26 are summarized in the following Table 4 together with corresponding IR and NMR data and melting points.

TABLE 4

$$Q-SO_2-N\underset{O}{\overset{O}{\diagup\diagdown}}NH$$

| Ex. No. | Q | IR(KBr,cm$^{-1}$) | NMR (DMSO-d$_6$,ppm) | M.P. (°C.) |
|---|---|---|---|---|
| 28 | 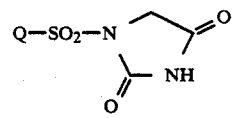 | 1803,1755, 1516,1372, 1350,1165 | 4.55(2H,s), 7.86~9.10(6H,m), 11.62(1H,bs) | 284.6 (dec.) |

TABLE 4-continued

Q—SO₂—N(CH₂C(=O)NHC(=O))

| Ex. No. | Q | IR(KBr,cm⁻¹) | NMR (DMSO-d₆,ppm) | M.P. (°C.) |
|---|---|---|---|---|
| 29 | 5-fluorobenzo[b]thiophen-2-yl | 1735, 1508, 1382, 1167 | 4.47(2H,s), 7.40~8.30(3H,m), 8.30(1H,s), 11.73(1H,bs) | 275.2 (dec.) |
| 30 | 5-chlorobenzo[b]thiophen-2-yl | 1739, 1380, 1192 | 4.45(2H,s), 7.57~7.69(1H,m), 8.15~8.25(2H,m), 8.29(1H,s), 11.70(1H,bs) | >300 |
| 31 | 3-chlorobenzo[b]thiophen-2-yl | 1728, 1381, 1183, 1162 | 4.64(2H,s), 7.58~7.81(2H,m), 7.96~8.06(1H,m), 8.18~8.29(1H,m), 11.82(1H,bs) | 278.3 (dec.) |
| 32 | 4-chlorobenzo[b]thiophen-2-yl | 3270, 1741, 1379, 1162 | 4.51(2H,s), 7.52~7.67(2H,m), 8.16~8.23(2H,m), 11.74(1H,bs) | 271.1~272.2 |
| 33 | 5-bromobenzofuran-2-yl | 3400, 1730, 1663, 1614, 1380, 1169 | 3.96(2H,s), 7.61~8.06(4H,m) | 270.2 (dec.) |
| 34 | 5-chlorobenzofuran-2-yl | 3379, 1616, 1608, 1381, 1233, 1166, | 3.98(2H,s), 7.47~7.90(4H,m) | 290.0 (dec.) |
| 35 | 2-methyl-6-methylbenzothiazol-? (6-methyl-2-methylbenzothiazol-yl) | 1740, 1376, 1166 | 2.88(3H,s), 4.53(2H,s), 8.10(2H,s), 8.80(1H,s), 11.59(1H,bs) | 258.0 (dec.) |
| 36 | benzimidazol-2-yl | 3328, 1740, 1390, 1159 | 4.60(2H,s), 7.33~7.78(5H,m), 11.85(1H,bs) | 222.8 (dec.) |
| 37 | benzo[b]thiophen-3-yl | 1741, 1380, 1162 | 4.54(2H,s), 7.52~7.63(2H,m), 8.10~8.29(2H,m), 8.86(1H,s), 11.58(1H,bs) | 218.3~226.7 |
| 38 | benzo[d]isothiazol-3-yl | 1739, 1377, 1165 | 4.49(2H,s), 7.50~8.28(4H,m), 11.68(1H,bs) | 237.8~243.0 |

TABLE 4-continued
$$Q-SO_2-N\begin{pmatrix}CH_2-C=O\\ \\ C=O\end{pmatrix}NH$$
| Ex. No. | Q | IR(KBr,cm$^{-1}$) | NMR (DMSO-d$_6$,ppm) | M.P. (°C.) |
|---|---|---|---|---|
| 39 | 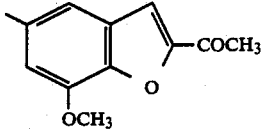 | 1746,1682, 1363,1158 | 2.59(3H,s), 4.07(3H,s), 4.51(2H,s), 7.57~8.13(3H,m), 11.55(1H,bs) | 263.0 (dec.) |
| 40 | 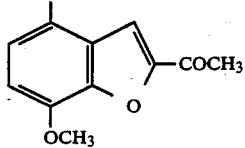 | 1735,1691, 1387,1173 | 2.63(3H,s), 4.10(3H,s), 4.54(2H,s), 7.36(1H,d,J=8.6Hz), 8.02(2H,m), 11.56(1H,bs) | 242.3~244.1 |
| 41 | 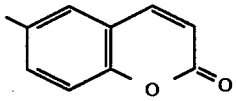 | 1803,1746, 1716,1377, 1164 | 4.51(2H,s), 6.64(1H,d,J=9.9Hz), 7.62(1H,d,J=8.9Hz), 8.11~8.46(3H,m), 11.60(1H,bs) | 262.8~267.8 |
| 42 | 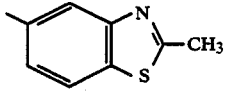 | 1741,1371, 1169 | 2.87(3H,s), 4.55(2H,s), 7.95~8.51(3H,m), 11.59(1H,bs) | 245.2~246.3 |
| 43 | 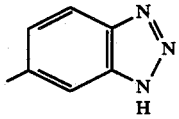 | 1741,1362, 1168 | 4.55(2H,s), 8.12(2H,s), 8.82(1H,s), 12.67(1H,bs) | |
| 44 | 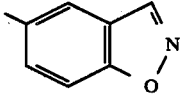 | 3098,1743, 1385,1364, 1186,1162, 1067 | 4.52(2H,s), 7.99~8.66(3H,m), 9.45(1H,d,J=1.0Hz), 11.59(1H,bs) | 203 (dec.) |
| 45 | 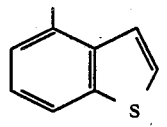 | 3095,1741, 1373,1360, 1177,1150 | 4.56(2H,s), 7.51~8.51(5H,m), 11.59(1H,bs) | 238.7~244.9 |
| 46 | 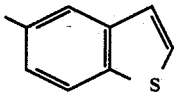 | 1729,1362, 1166 | 4.54(2H,s), 7.66~8.59(5H,m), 11.56(1H,bs) | 268.4~271.4 |
| 47 | 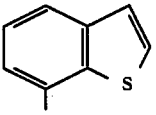 | 3174,1735, 1390,1170 | 4.61(2H,s), 7.57~7.74(2H,m), 7.95~8.34(3H,m), 11.55(1H,bs) | 242.9~244.3 |
| 48 | 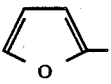 | 1800,1742, 1396,1162 | 4.43(2H,s), 6.78(1H,m), 7.45(1H,d,J=3.6Hz), 8.09(1H,m), 11.72(1H,bs) | 243.0~244.2 |
| 49 | 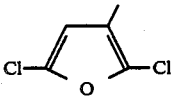 | 3227,1735, 1365,1183, 1171 | 4.51(2H,s), 7.55(1H,s), 11.76(1H,bs) | 251.2~251.3 |

TABLE 4-continued

Q—SO$_2$—N⟨structure with NH and two C=O⟩

| Ex. No. | Q | IR(KBr, cm$^{-1}$) | NMR (DMSO-d$_6$, ppm) | M.P. (°C.) |
|---|---|---|---|---|
| 50 | 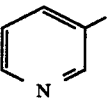 (3-pyridyl) | 1742, 1375, 1174 | 4.53(2H,s), 7.71(1H,m), 8.40(1H,m), 8.89~9.14(2H,m), 11.65(1H,bs) | 175.5 (dec.) |
| 51 | CH$_3$— | 1744, 1384, 1359, 1164, 1153 | 3.35(3H,s), 4.33(2H,s), 11.65(1H,bs) | 196.2~198.3 |
| 52 | 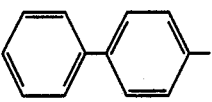 (biphenyl) | 1749, 1727, 1371, 1170 | 4.55(2H,s), 7.38~8.16(9H,m), 11.63(1H,bs) | 261.0~261.5 |

EXAMPLE 53

Preparation of 1-(4,5-diphenylthiophen-2-ylsulfonyl)hydantoin.

Step 1

Preparation of N-(4,5-diphenylthiophen-2-ylsulfonyl)glycine ethyl ester.

To a suspension of 4,5-diphenylthiophen-2-ylsulfonyl chloride (36.5 g) and glycine ethyl ester hydrochloride (30.4 g) in dichloromethane (320 ml) was added slowly triethylamine (3.03 ml) under ice-cooling, and the mixture was stirred for 160 minutes at room temperature. Water (200 ml) was added to the resultant solution, and extracted with dichloromethane. The organic layer was washed successively with 1N hydrochloric acid, water and saturated aqueous NaCl solution, and dried over anhydrous magnesium sulfate. Dichloromethane was removed in vacuo, and the residue was reprecipitated from ethyl acetate and hexane to give 41.1 g of the objective compound.

Melting point: 151.2°–152.7° C.

IR (KBr, cm$^{-1}$): 3266, 1734, 1354, 1231, 1215, 1164, 1127

NMR (DMSO-d$_6$, ppm): 1.12 (3H, t, J=7.1 Hz), 3.88 (2H, d, J=6.3 Hz), 4.04 (2H, q, J=7.1 Hz), 6.84–7.44 (10H, m), 7.67 (1H, s), 8.57 (1H, t, J=6.3 Hz)

Step 2

Preparation of N-(4,5-diphenylthiophen-2-ylsulfonyl)glycine.

A solution of sodium hydroxide (12.4 g) in water (73 ml) was added to a solution of the product obtained in Step 1 (41.4 g) in tetrahydrofuran (730 ml), and the mixture was stirred for 25 minutes at 60° C. After removing the solvent, water (300 ml) was added to the residue, and the resultant solution was acidified with concentrated hydrochloric acid to a pH 1 under ice-cooling. The acidified solution was extracted thrice with ethyl acetate (800 ml), the organic layer was washed with water, then with saturated aqueous NaCl solution, and dried over anhydrous sodium sulfate. Ethyl acetate was removed in vacuo, the residue was reprecipitated from ethyl acetate and hexane to give 37.6 g of the objective compound.

Melting point: 172.2°–174.4° C.

IR (KBr, cm$^{-1}$): 3268, 1736, 1353, 1159

NMR (DMSO-d$_6$, ppm): 3.78 (2H, d, J=5.9 Hz), 7.12–7.42 (10H, m), 7.67 (1H, s), 8.39 (1H, t, J=5.9 Hz), 12.78 (1H, bs)

Step 3

Preparation of 1-(4,5-diphenylthiophen-2-ylsulfonyl)-2-thiohydantoin.

Starting from the product obtained in Step 2, the objective compound was obtained in a manner similar to Step 2 of Example 1.

Melting point: 213.2°–215.4° C.

IR (KBr, cm$^{-1}$): 1752, 1446, 1376, 1168, 1083

NMR (DMSO-d$_6$, ppm): 4.77 (2H, s), 7.32–7.46 (10H, m), 8.12 (1H, s), 12.73 (1H, bs)

Step 4

Preparation of 1-(4,5-diphenylthiophen-2-ylsulfonyl)hydantoin.

Starting from the product obtained in Step 3, the objective compound was obtained in a manner similar to Step 3 of Example 26.

Melting point: 242.5°–243.9° C.

IR (KBr, cm$^{-1}$): 1737, 1386, 1165

NMR (DMSO-d$_6$, ppm): 4.53 (2H, s), 7.32–7.45 (10H, m), 8.00 (1H, s), 11.72 (1H, bs)

Compounds of Example 54 and 55 prepared in a manner similar to Example 53 are summarized in the following Table 5 together with corresponding IR and NMR data and melting points.

TABLE 5

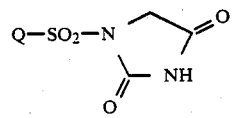

| Ex. No. | Q | IR(KBr,cm$^{-1}$) | NMR(DMSO-d$_6$,ppm) | M.P. (°C.) |
|---|---|---|---|---|
| 54 | (cyclohexyl-H) | 1721,1367, 1349,1172, 1161 | 0.96~2.40(10H,m), 3.30~3.69(1H,m), 4.31(2H,s), 11.61(1H,bs) | 154.9~ 156.7 |
| 55 | H$_3$C~(long chain) | 1735,1725, 1359,1163 | 0.69~1.98(15H,m), 3.42~3.59(2H,m), 4.33(2H,s), 11.64(1H,bs) | 141.3~ 143.2 |

EXAMPLE 56

Preparation of 1-(5-nitrobenzo[b]thiophen-2-ylsulfonyl)hydantoin.

Step 1

Preparation of N-(5-nitrobenzo[b]thiophen-2-ylsulfonyl)glycine.

Starting from 5-nitrobenzo[b]thiophen-2-ylsulfonyl chloride, the objective compound was obtained in a manner similar to Step 1 of Example 1.

Melting point: 187.2°–194.8° C.

IR (KBr, cm$^{-1}$): 3325, 1734, 1530, 1377, 1351, 1159

NMR (DMSO-d$_6$, ppm): 3.76 (2H, d, J=5.9 Hz), 8.22 (1H, s), 8.32–8.91 (4H, m), 12.72 (1H, bs)

Step 2

Preparation of 1-(5-nitrobenzo[b]thiophen-2-ylsulfonyl)-2-thiohydantoin.

Starting from the product obtained in Step 1, the objective compound was obtained in a manner similar to Step 2 of Example 1.

Melting point: 217.4° C. (decomposition)

IR (KBr, cm$^{-1}$): 1762, 1521, 1470, 1389, 1347, 1248, 1173, 1087

NMR (DMSO-d$_6$, ppm): 4.73 (2H, s), 8.25–9.09 (4H, m), 12.78 (1H, bs)

Step 3

Preparation of 1-(5-nitrobenzo[b]thiophen-2-ylsulfonyl)hydantoin.

A mixture of the product obtained in Step 2 (1.66 g) and 50% (w/v) nitric acid (35 ml) was heated with stirring for 6 hours at 60° C., and the resultant solution was poured into ice-water (150 ml). The formed precipitate was separated by filtration and washed with acetone to give 0.47 g of the objective compound.

Melting point: 282.4° C. (decomposition)

IR (KBr, cm$^{-1}$): 3100, 1737, 1522, 1385, 1349 1176

NMR (DMSO-d$_6$, ppm): 4.47 (2H, s), 8.22–9.05 (4H, m), 11.70 (1H, bs)

EXAMPLE 57

Preparation of 1-(5-cyanobenzo[b]thiophen-2-ylsulfonyl)hydantoin.

Step 1

Preparation of N-(5-cyanobenzo[b]thiophen-2-ylsulfonyl)glycine.

Starting from 5-cyanobenzo[b]thiophen-2-ylsulfonyl chloride, the objective compound was obtained in a manner similar to Step 1 of Example 1.

IR (KBr, cm$^{-1}$): 3289, 2235, 1714, 1350, 1153

NMR (DMSO-d$_6$, ppm): 3.75 (2H, d, J=5.6 Hz), 7.87 (1H, dd, J=8.6, 1.3 Hz), 8.06 (1H, s), 8.34 (1H, d, J=8.6 Hz), 8.56 (1H, d, J=1.3 Hz), 8.70 (1H, t, J=5.6 Hz), 12.69 (1H, bs)

Step 2

Preparation of 1-(5-cyanobenzo[b]thiophen-2-ylsulfonyl)-2-thiohydantoin.

Starting from the product obtained in Step 1, the objective compound was obtained in a manner similar to Step 2 of Example 1.

IR (KBr, cm$^{-1}$): 2231, 1762, 1451, 1451, 1243, 1173, 1077

NMR (DMSO-d$_6$, ppm): 4.73 (2H, s), 7.95 (1H, dd, J=8.6, 1.7 Hz), 8.41 (1H, d, J=8.6 Hz), 8.53 (1H, s), 8.63 (1H, d, J=1.7 Hz), 12.72 (1H, bs)

Step 3

Preparation of 1-(5-cyanobenzo[b]thiophen-2-ylsulfonyl)hydantoin.

A mixture of the product obtained in Step 2 (0.39 g) and 50% (w/v) nitric acid (8.2 ml) was heated with stirring for 5 minutes at 80° C., then for 30 minutes at room temperature, and the resultant solution was poured into ice-water (35 ml). The formed precipitate was separated by filtration and washed with acetone (100 ml) to give 0.11 g of the objective compound.

Melting point: 276.3° C. (decomposition)

IR (KBr, cm$^{-1}$): 3100, 2231, 1740, 1386, 1172

NMR (DMSO-d$_6$, ppm): 4.47 (2H, s), 7.95 (1H, dd, J=8.6, 1.7 Hz), 8.41 (1H, s), 8.42 (1H, d, J=8.6 Hz), 8.65 (1H, d, J=1.7 Hz), 11.75 (1H, bs)

EXAMPLE 58

Preparation of 1-(5-carboxybenzo[b]thiophen-2-ylsulfonyl)hydantoin.

To the suspension of the product obtained in Step 3 of Example 57 (0.1 g) in water (1.5 ml) was added slowly concentrated sulfuric acid (1.5 ml) and acetic acid (1.5 ml) under ice-cooling, and the mixture was stirred under reflux for 2 hours. After cooling to room temperature, the formed precipitate was separated by filtration and washed with acetone (20 ml). The washings were concentrated in vacuo, and the residue was triturated with ether (2 ml) to give 0.02 g of the objective compound.

Melting point: >300° C.

IR (KBr, cm$^{-1}$): 1743, 1690, 1380, 1163

NMR (DMSO-d$_6$, ppm): 4.46 (2H, s), 8.07 (1H, dd, J=8.6, 1.7 Hz), 8.28 (1H, d, J=8.6 Hz), 8.48 (1H, s), 8.69 (1H, d, J=1.7 Hz)

EXAMPLE 59

Preparation of 1-(indol-2-ylsulfonyl)hydantoin.

Step 1

Preparation of N-(1-benzenesulfonylindol-2-ylsulfonyl)glycine ethyl ester.

Starting from 1-benzenesulfonylindol-2-ylsulfonyl chloride, the objective compound was obtained in a manner similar to Step 1 of Example 53.

IR (KBr, cm$^{-1}$): 3335, 1746, 1346, 1338, 1171

NMR (DMSO-d$_6$, ppm): 1.11 (3H, t, J=7.3 Hz), 3.94 (2H, d, J=5.6 Hz), 4.06 (2H, q, J=7.3 Hz), 6.38 (1H, t, J=5.6 Hz), 7.14–8.32 (10H, m)

Step 2

Preparation of N-(indol-2-ylsulfonyl)glycine.

A solution of sodium hydroxide (1.6 g) in water (7 ml) was added to a solution of the product obtained in Step 1 (4.22 g) in tetrahydrofuran (70 ml) at room temperature, and the mixture was stirred for 5 minutes at 65°–75° C. After removing tetrahydofuran in vacuo, a solution of sodium hydroxide (0.4 g) in water (23 ml) was added to the residue, and the mixture was stirred for 5 hours at 65°–75° C. After cooling to room temperature, the resultant solution was washed with ether, acidified with 6N hydrochloric acid to a pH 1 under ice-cooling, and extracted with ethyl acetate (15 ml×3). The organic layer was washed with water and saturated aqueous NaCl solution, and dried over anhydrous sodium sulfate. Ethyl acetate was removed in vacuo, and the residue was triturated with ethyl acetate and hexane to give 1.66 g of the objective compound.

Melting point: 170.2°–171.9° C.

IR (KBr, cm$^{-1}$): 3328, 1707, 1340, 1155, 1145

NMR (DMSO-d$_6$, ppm): 3.73 (2H, d, J=6.3 Hz), 6.94–7.70 (5H, m), 8.05 (1H, t, J=6.3 Hz), 11.90 (1H, bs), 12.67 (1H, bs)

Step 3

Preparation of 1-(indol-2-ylsulfonyl)-2-thiohydantoin.

Starting from the product obtained in Step 2, the objective compound was obtained in a manner similar to Step 2 of Example 1.

Melting point: 209.2°–210.4° C.

IR (KBr, cm$^{-1}$): 3131, 3103, 1755, 1473, 1367, 1249, 1197, 1165, 1147, 1079

NMR (DMSO-d$_6$, ppm): 4.81 (2H, s), 7.08–7.78 (5H, m), 12.33 (1H, bs), 12.66 (1H, bs)

Step 4

Preparation of 1-(indol-2-ylsulfonyl)hydantoin.

Starting from the product obtained in Step 3, the objective compound was obtained in a manner similar to Step 3 of Example 26.

Melting point: 287.1° C. (decomposition)

IR (KBr, cm$^{-1}$): 3290, 1787, 1725, 1389, 1365, 1156

NMR (DMSO-d$_6$, ppm): 4.67 (2H, s), 7.29–7.58 (5H, m), 11.67 (1H, bs), 12.63 (1H, bs)

EXAMPLE 60

Preparation of 1-(2-carboxychromon-6-ylsulfonyl)hydantoin.

Step 1

Preparation of N-(2-methoxycarbonylchromon-6-ylsulfonyl)glycine.

To a suspension of 2-methoxycarbonylchromon-6-ylsulfonyl chloride (20.0 g) in acetone (600 ml) was added slowly a solution of glycine (6.15 g), sodium hydroxide (3.28 g) and sodium bicarbonate (6.11 g) in water (300 ml), and the mixture was stirred for 85 minutes at room temperature. After adjusting a pH of the resultant solution to ca. 6 with 6N hydochloric acid, acetone was removed in vacuo, and insoluble matters were filtered off. The filtrate was acidified with 2N hydrochloric acid to a pH 1 under ice-cooling. The acidified solution was extracted with ethyl acetate (350 ml×3), the organic layer was washed with water, then saturated aqueous NaCl solution, and dried over anhydrous sodium sulfate. Ethyl acetate was removed in vacuo, the residue was purified by silica-gel column chromatography to give 5.45 g of the objective compound.

Melting point: 210.6°–212.8° C.

IR (KBr, cm$^{-1}$): 3327, 1746, 1716, 1659, 1288, 1266, 1165

NMR (DMSO-d$_6$, ppm): 3.67 (2H, d, J=5.9 Hz), 3.96 (3H, s), 7.04 (1H, s), 7.89–8.42 (4H, m)

Step 2

Preparation of 1-(2-methoxycarbonylchromon-6-ylsulfonyl)-2-thiohydantoin.

Starting from the product obtained in Step 1, the objective compound was obtained in a manner similar to Step 2 of Example 1.

Melting point: 217.4° C. (decomposition)

IR (KBr, cm$^{-1}$): 1746, 1660, 1443, 1374, 1282, 1260, 1174

NMR (DMSO-d$_6$, ppm): 3.96 (3H, s), 4.84 (2H, s), 7.07 (1H, s), 7.97–8.71 (3H, m), 12.68 (1H, bs)

Step 3

Preparation of 1-(2-methoxycarbonylchromon-6-ylsulfonyl)hydantoin.

Starting from the product obtained in Step 2, the objective compound was obtained in a manner similar to Step 3 of Example 26.

Melting point: >300° C.

IR (KBr, cm$^{-1}$): 1751, 1741, 1664, 1617, 1375, 1177,

NMR (DMSO-d$_6$, ppm): 3.96 (3H, s), 4.52 (2H, s) 7.07 (1H, s), 7.98–8.64 (3H, m)

Step 4

Preparation of 1-(2-carboxychromon-6-ylsulfonyl)hydantoin.

A solution of the product obtained in Step 3 (2.27 g) in a saturated aqueous sodium bicarbonate solution (22.7 ml) was stirred for 2 hours at 40° C. The resultant solution was washed with ethyl acetate and acidified with 2N hydrochloric acid to a pH 1 under ice-cooling, and the formed precipitate was separated by filtration to give 0.82 g of the objective compound.

Melting point: 279.3° C. (decomposition)

IR (KBr, cm$^{-1}$): 3220, 1751, 1663, 1376, 1172

NMR (DMSO-d$_6$, ppm): 4.54 (2H, s), 7.02 (1H, s), 7.95–8.61 (3H, m), 11.63 (1H, bs)

EXAMPLE 61

Preparation of 1-(benzothiazol-2-ylsulfonyl)hydantoin (compound 22).

Step 1

Preparation of N-(benzothiazol-2-ylsulfonyl)glycinamide.

To a suspension of glycinamide hydrochloride (43 g) in dioxane (1 l) was added benzothiazol-2-ylsulfonyl chloride (90.9 g) under ice-cooling, and a pH of the mixture was adjusted to 8 with saturated aqueous sodium carbonate solution. After stirring for 1.5 hours, the resultant solution was concentrated in vacuo. Water (1.5 l) was added to the residue, and the solution was acidified with concentrated hydrochloric acid to pH 2. The formed precipitate was separated by filtration to give 59.8 g of the objective compound.

Melting point: 179.7°–181.8° C.
IR (KBr, cm$^{-1}$): 3426, 1682, 1346, 1165
NMR (DMSO-$d_6$, ppm): 3.73 (2H, s), 7.08 (1H, bs), 7.36 (1H, bs), 7.52–8.29 (4H, m), 8.80 (1H, bs)

Step 2

Preparation of N-(benzothiazol-2-ylsulfonyl)N-methoxycarbonylglycinamide.

To a solution of the product obtained in Step 1 (102.3 g) in N,N-dimethylformamide (1.2 l) was added slowly 60% sodium hydride (16.7 g) under ice-cooling, and the mixture was stirred for 1 hour at room temperature. Methyl chlorocarbonate (35.8 g) was added to the above-mentioned mixture followed by stirring for 1 hour at room temperature. After removing the solvent, water (3.5 l) was added to the residue, and the formed precipitate was separated by filtration to give 60.5 g of the objective compound.

Melting point: 153.1° C. (decomposition)
IR (KBr, cm$^{-1}$): 3459, 3346, 1737, 1689, 1386, 1343, 1250, 1171
NMR (DMSO-$d_6$, ppm): 3.70 (3H, s), 4.51 (2H, s), 7.30 (1H, bs), 7.60–7.76 (3H, m), 8.20–8.39 (2H, m)

Step 3

Preparation of 1-(benzothiazol-2-ylsulfonyl)hydantoin.

To a solution of the product obtained in Step 2 (20.0 g) in N,N-dimethylformamide (200 ml) added slowly 60% sodium hydride (2.67 g), and the mixture was stirred for 13.5 hours at 70° C. After removing the solvent, water (1 l) was added to the residue, and the solution was extracted with ethyl acetate (1.5 l). The organic layer was washed with saturated aqueous NaCl solution, and dried over anhydrous sodiumسسsulfate. Ethyl acetate was removed in vacuo, and the residue was washed with acetone-chloroform (100 ml + 200 ml) to give 2.12 g of the objective compound.

Melting point: 260.4°–261.9° C.
IR (KBr, cm$^{-1}$): 3200, 3105, 1739, 1393, 1355, 1173
NMR (DMSO-$d_6$, ppm): 4.55 (2H, s), 7.61–7.81 (2H, m), 8.18–8.40 (2H, m), 11.88 (1H, bs)

EXAMPLE 62

Preparation of 1-(benzo[c]thiophen-1-ylsulfonyl)hydantoin.

Step 1

Preparation of N-(benzo[c]thiophen-1-ylsulfonyl)glycinamide.

To a suspension of lithium benzo[c]thiophen-1-sulfinate (8.3 g) in isopropanol (200 ml) and water (200 ml) was added N-chlorosuccinimide (6.5 g) at 0° C. After stirring for 30 minutes at 0° C., N-chlorosuccinimide (1.63 g) was added, and the mixture was stirred for additional 1 hour. The resultant solution was extracted with dichloromethane (1 l×2), and the organic layer was washed with water, then saturated aqueous NaCl solution. After drying over anhydrous sodium sulfate, dichloromethane was removed in vacuo under cooling. Using this residue and glycinamide hydrochloride, the objective compound was obtained in a manner similar to Step 1 of Example 61.

NMR (DMSO-$d_6$, ppm): 3.40 (2H, d, J=6.9 Hz), 7.06–8.22 (5H, m), 8.49 (1H, s)

Step 2

Preparation of N-(benzo[c]thiophen-1-ylsulfonyl)N$^2$-methoxycarbonylglycinamide.

To a solution of the product obtained in Step 1 (0.45 g) in N,N-dimethylformamide (5 ml) was added slowly 60% sodium hydride (75 mg) under ice-cooling, and the mixture was stirred for 30 minutes at room temperature. Methyl chloroformate (0.14 ml) was added to the above-mentioned mixture followed by stirring for 20 minutes at room temperature. 60% sodium hydride (75 mg) was added to the solution, and the mixture was stirred for 1.5 hours at room temperature, then 15 minutes at 70° C. After cooling to room temperature, water (20 ml) was added to the resultant mixture and this aqueous solution was extracted with ethyl acetate (20 ml×3). The organic layer was washed with water, then saturated aqueous NaCl solution. After drying over anhydrous magnesium sulfate, ethyl acetate was removed in vacuo and the residue was purified by silica-gel column chromatography to give 0.18 g of the objective compound.

NMR (CDCl$_3$, ppm): 3.74 (3H, s), 4.24 (2H, d, J=5.3 Hz), 5.92 (1H, t, J=5.3 Hz), 7.17–8.31 (6H, m)

Step 3

Preparation of 1-(benzo[c]thiophen-1-ylsulfonyl)-hydantoin.

To a solution of the product obtained in Step 2 (0.18 g) in N,N-dimethylformamide (3 ml) added slowly 60% sodium hydride (48 mg), and the mixture was stirred for 2.5 hours at 70° C. After removing the solvent, ice water (20 ml) was added to the residue, and pH of the solution was adjusted to 4 with 1N hydrochloric acid. The resultant solution was extracted with ethyl acetate (20 ml×3), and the organic layer was washed with saturated aqueous NaCl solution, and dried over anhydrous magnesium sulfate. Ethyl acetate was removed in vacuo, and the residue was triturated with dichloromethane to give 0.03 g of the objective compound.

Melting point: 223.6°–226.9° C.
IR (KBr, cm$^{-1}$): 1736, 1378, 1185, 1162, 1152
NMR (DMSO-$d_6$, ppm): 4.51 (2H, s), 7.20–8.16 (4H, m), 8.82 (1H, s), 11.54 (1H, bs)

Intermediate compounds of Examples 6 to 25, 28 to 52, 54 and 55 are summarized to the following tables 6 and 7 together with corresponding IR and NMR data and melting points.

TABLE 6
Q—SO₂NHCH₂CO₂H
| Ex. No. | Q | IR(KBr, cm⁻¹) | NMR (DMSO-d₆, ppm) | M.P. (°C.) |
|---|---|---|---|---|
| 6 | 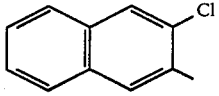 | 3345,1710, 1315,1140 | 3.69 (2H, d), 7.61~8.37 (6H, m), 8.49 (1H, s) | 174.5~ 182.1 |
| 7 | 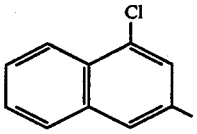 | | 3.70 (2H, d, J=5.9Hz), 7.72~8.50 (7H, m) | 185.2~ 186.4 |
| 8 | 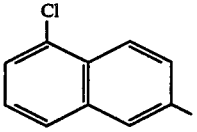 | | 3.44 (2H, s), 7.52~8.60 (7H, m) | >300 |
| 9 | 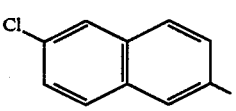 | 3350,1715, 1320,1145 | 3.55 (2H, d, J=5.8Hz), 7.51~8.30(6H, m), 8.48 (1H, s) | 158.8~ 165.7 |
| 10 | 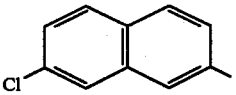 | | 3.73 (2H, s), 7.51~8.53 (7H, m) | 247.8~ 254.7 |
| 11 | 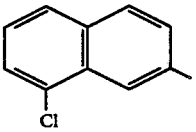 | | 3.69 (2H, d, J=6.0Hz), 7.58~8.71 (7H, m) | 157.8~ 162.1 |
| 12 | 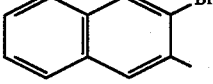 | 3345,1715, 1330,1165 | 3.78(2H, d, J=5.9Hz), 7.61~8.22(5H, m), 8.42(1H, s), 8.64(1H, s) | 210.0~ 214.4 |
| 13 | 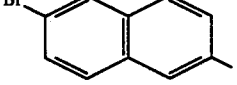 | 3350,1715, 1320,1145 | 3.48(2H, s), 7.52~8.48(7H, m) | 257.2~ 265.7 |
| 14 | 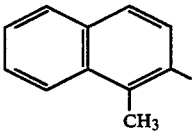 | | 2.98(3H, s), 3.62(2H,d, J=5.9Hz), 7.52~8.35(7H, m) | 179.0~ 182.7 |
| 15 | 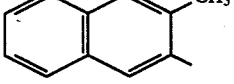 | | 2.79(3H, s), 3.73(2H, d, J=6.1Hz), 7.43~8.35(6H,m), 8.53(1H, s) | 155.5~ 160.5 |
| 16 | 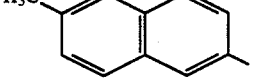 | | 2.49(3H, s), 3.40(2H, s), 7.35~8.39(7H, m) | 225.7~ 230.6 |
| 17 | 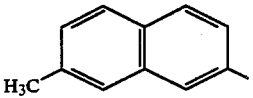 | | 2.49(3H, s), 3.65(2H, s), 7.35~8.45(7H, m) | 147.4~ 152.0 |

TABLE 6-continued
Q—SO₂NHCH₂CO₂H
| Ex. No. | Q | IR(KBr, cm⁻¹) | NMR (DMSO-d₆, ppm) | M.P. (°C.) |
|---|---|---|---|---|
| 18 | 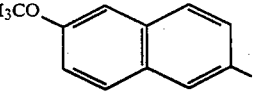 | 3340,1710, 1325,1155 | 3.62(2H, d, J=6.0Hz), 3.91(3H, s), 7.19~8.15(6H, m), 8.31(1H, s) | 161.4~ 163.6 |
| 19 | 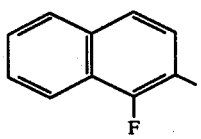 |  | 3.78(2H, d, J=5.9Hz), 7.67~8.45(7H, m) | 163.5~ 168.5 |
| 20 | 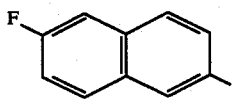 |  | 3.62(2H, s), 7.05~8.50(7H, m) | 109.0~ 109.5 |
| 21 | 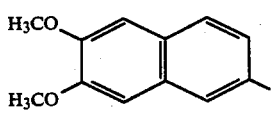 |  | 3.55(2H, s), 3.93(6H, s), 7.35~7.98(5H, m), 8.24(1H, s) | 212.6~ 217.1 |
| 22 | 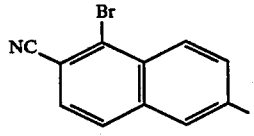 | 3280,2230, 1760,1155 | 3.71(2H, d, J=6.0Hz), 7.87~8.65(6H, m) | 231.9~ 234.9 |
| 23 | 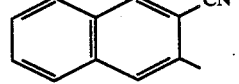 | 3260,2240, 1740,1155 | 3.69(2H, d, J=6.0Hz), 7.82~8.73(7H, m) | 186.2~ 192.0 |
| 24 | 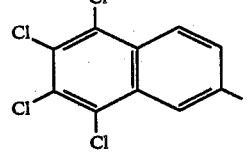 |  | 3.72(2H, d, J=5.7Hz), 8.09~8.68(4H, m) | 258.8~ 261.5 |
| 25 | 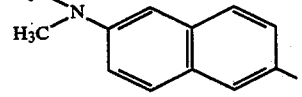 |  | 3.06(6H, s), 3.55(2H, d, J=6.0Hz), 6.91~8.21(7H, m) | 148.0~ 152.0 |
| 28 | 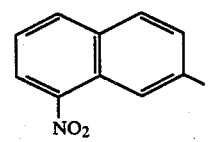 | 3348,1710, 1518,1334, 1142 | 3.68(2H, d, J=6.3Hz), 7.78~8.89(7H, m), 12.63(1H, bs) | 224.9~ 227.7 |
| 29 | 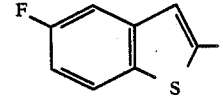 | 3290,1709, 1342,1156 | 3.73(2H, d, J=5.9Hz), 7.31~8.22(4H, m), 8.59(1H, t, J=5.9Hz), 12.72(1H, bs) | 162.7~ 164.2 |
| 30 | 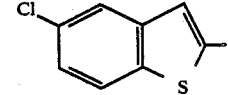 | 3295,1709, 1343,1156 | 3.73(2H, d, J=5.9Hz), 7.49~8.17(4H, m), 8.59(1H, t, J=5.9Hz), 12.54(1H, bs) | 186.9~ 189.1 |

TABLE 6-continued

Q—SO$_2$NHCH$_2$CO$_2$H

| Ex. No. | Q | IR(KBr, cm$^{-1}$) | NMR (DMSO-d$_6$, ppm) | M.P. (°C.) |
|---|---|---|---|---|
| 31 | 3-chloro-2-methylbenzo[b]thiophen-2-yl | 3337,1716, 1342,1257, 1162 | 3.83(2H, d, J=6.3Hz), 7.52~8.24(4H, m), 8.87(1H, t, J=6.3Hz), 12.63(1H, bs) | 156.6~ 161.0 |
| 32 | 4-chloro-2-methylbenzo[b]thiophen-2-yl | 3255,1710, 1356,1248, 1160 | 3.78(2H, d, J=5.9Hz), 7.44~8.13(4H, m), 8.66(1H, t, J=5.9Hz), 12.68(1H, bs) | 197.0~ 199.2 |
| 33 | 5-bromo-2-methylbenzofuran-2-yl | 3334,1717, 1437,1352, 1241,1152 | 3.78(2H, s), 7.49(1H, s) 7.68(2H, s), 8.00(1H, s), 8.83(1H, bs) | 192.4~ 194.1 |
| 34 | 5-chloro-2-methylbenzofuran-2-yl | 3377,1718, 1358,1247, 1157 | 3.76(2H, s), 7.44~7.89(4H, m) | 191.5~ 193.8 |
| 35 | 2,6-dimethylbenzothiazol-2-yl | 3290,1720, 1340,1170 | 2.86(3H, s), 3.63(2H, d, J=6.3Hz), 7.79~8.54(4H, m), 12.48(1H, bs) | 237.7 (dec.) |
| 36 | 2-methylbenzimidazol-2-yl | 3068,1718, 1617,1349, 1155 | 3.78(2H, s), 7.25~7.70(4H, m) | 133.5~ 135.9 |
| 37 | 3-methylbenzo[b]thiophen-2-yl | 3318,1724, 1339,1241, 1152 | 3.64(2H, d, J=5.9Hz), 7.36~7.60(2H, m), 7.97~8.45(4H, m) | |
| 38 | 3-methylbenzo[d]isothiazol-2-yl | 3094,1721, 1348,1164 | 3.82(2H, s), 7.43~8.17(4H, m), 9.09(1H, bs), 12.51(1H, bs) | 212.5~ 214.4 |
| 39 | 3-acetyl-5-methyl-7-methoxybenzofuran-2-yl | 3290,1733, 1655,1331, 1158 | 2.58(3H, s), 3.61(2H, d, J=5.9Hz), 4.03(3H, s), 7.49~8.17(4H, m), 12.50(1H, bs) | 215.0~ 217.6 |
| 41 | 6-methyl-2H-chromen-2-on-yl | 3265,1748, 1711,1316, 1205,1154 | 3.65(2H, d, J=5.9Hz), 6.62(1H, d, J=9.9Hz), 7.57(1H, d, J=8.6Hz), 7.92~8.25(4H, m), 12.69(1H, bs) | 235.0 (dec.) |
| 42 | 2,5-dimethylbenzothiazol-2-yl | 3302,1727, 1330,1216, 1154 | 2.85(3H, s), 3.63(2H, d, J=5.9Hz), 7.73~8.29(4H, m) | 257.2 (dec.) |

TABLE 6-continued
Q—SO₂NHCH₂CO₂H
| Ex. No. | Q | IR(KBr, cm⁻¹) | NMR (DMSO-d₆, ppm) | M.P. (°C.) |
|---|---|---|---|---|
| 43 | 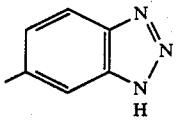 | 3213,1718, 1317,1255, 1164,1153 | 3.64(2H, d, J=5.6Hz), 7.78~8.38(4H, m) | 243.5~ 245.3 |
| 44 | 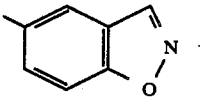 | 3271,1742, 1316,1149 | 3.64(2H, d, J=6.3Hz), 7.90~8.63(4H, m), 9.38(1H, s), 12.57(1H, bs) | 165.3~ 168.5 |
| 45 | 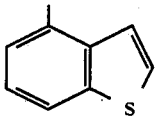 | 3097,1741, 1316,1209, 1148 | 3.57(2H, d, J=5.9Hz), 7.39~8.33(6H, m) | |
| 46 | 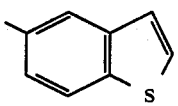 | 3186,1765, 1751,1732, 1335,1145 | 3.60(2H, d, J=6.3Hz), 7.61~8.35(6H, m), 12.58(1H, bs) | |
| 47 | 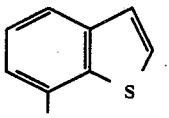 | 3282,1727, 1309,1161, 1137 | 3.65(2H, d, J=5.9Hz), 7.47~8.18(5H, m), 8.33(1H, t, J=5.9Hz), 12.64(1H, bs) | |
| 48 | 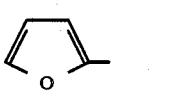 | 3307,1725, 1340,1329, 1157 | 3.66(2H, d, J=6.3Hz), 6.58~7.90(3H, m), 8.38(1H, t, J=6.3Hz), 12.63(1H, bs) | |
| 49 | 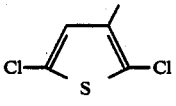 | 3358,1728, 1348,1236, 1166 | 3.76(2H, d, J=5.9Hz), 7.28(1H, s), 8.45(1H, t, J=5.9Hz), 12.76(1H, bs) | |
| 50 | 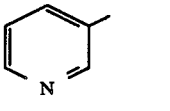 | 3236,1701, 1341,1174 | 3.70(2H, d, J=5.9Hz), 7.54~8.24(2H, m), 8.33(1H, t, J=5.9Hz), 8.76~8.96(2H, m), 12.70(1H, bs) | 220.4~ 223.8 |
| 51 | CH₃— | 3258,1711, 1320,1247, 1148 | 2.92(3H, s), 3.72(2H, d, J=5.9Hz), 7.39(1H, t, J=5.9Hz), 12.71(1H, bs) | 168.0~ 171.0 |
| 52 | 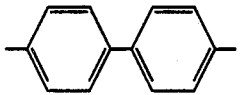 | 3348,1714, 1323,1152 | 3.62(2H, d, J=6.3Hz), 7.44~7.87(9H, m), 8.06(1H, t, J=6.3Hz) | |
| 54 |  | 3308,1714, 1319,1147, 1126 | 1.18~2.06(10H, m), 2.64~3.19(1H, m), 3.69(2H, d, J=6.0Hz), 7.33(1H, t, J=6.0Hz) | 96.0~ 100.9 |
| 55 | 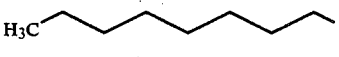 | 3314,3256, 2921,1716, 1313,1141 | 0.80~1.86(15H, m), 2.91~3.08(2H, m), 3.70(2H, d, J=5.9Hz), 7.39(1H, t, J=5.9Hz), 12.69(1H, bs) | |

TABLE 7
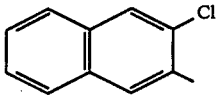
| Ex. No. | Q | IR(KBr, cm$^{-1}$) | NMR(DMSO-d$_6$, ppm) | M.P. (°C.) |
|---|---|---|---|---|
| 6 | 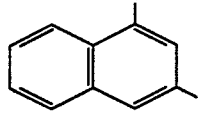 | 3130, 1785, 1760, 1165 | 4.90(2H, s), 7.69~8.45(5H, m), 8.88(1H, s) | 212.9 ~ 222.8 |
| 7 | 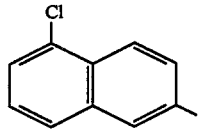 | | 4.88(2H, s), 7.74~8.83(6H, m) | 250.1 (dec.) |
| 8 | 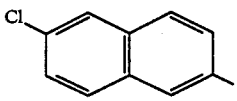 | | 4.89(2H, s), 7.59~8.43(5H, m), 8.70~8.96(1H, m) | 231.4 (dec.) |
| 9 | 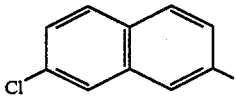 | 3150, 1795, 1770, 1170 | 4.93(2H, s), 7.61~8.35(5H, m), 8.89(1H, s) | 211.4 ~ 221.9 |
| 10 | 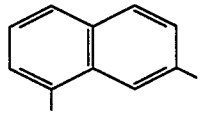 | | 4.88(2H, s), 7.68~8.39(5H, m), 8.80(1H, s) | 227.8 (dec.) |
| 11 | 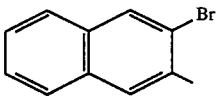 | | 4.89(2H, s), 7.60~8.29(5H, m), 8.69~8.87(1H, m) | 190.5 (dec.) |
| 12 | 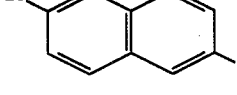 | 3270, 1795, 1770, 1170 | 4.94(2H, s), 7.65~8.51(5H, m), 8.99(1H, s) | 248.5 ~ 255.7 |
| 13 | 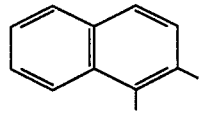 | 3120, 1785, 1755, 1165 | 4.85(2H, s), 7.70~8.40(5H, m), 8.67~8.84(1H, m) | 198.5 ~ 209.5 |
| 14 | 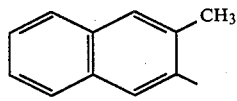 | | 2.97(3H, s), 4.86(2H, s), 7.55~8.47(6H, m) | 243.9 (dec.) |
| 15 | 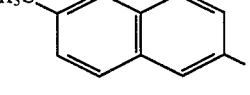 | | 2.64(3H, s), 4.80(2H, s), 7.47~8.26(5H, m), 8.81(1H, s) | 242.0 ~ 244.7 |
| 16 | H$_3$C-naphthyl | | 2.53(3H, s), 4.91(2H, s), 7.45~8.68(5H, m), 8.70(1H, s) | 234.8 ~ 237.6 |

TABLE 7-continued

Q-SO₂-N(C(=S))-CH₂-C(=O)-NH (hydantoin-like structure with thione)

| Ex. No. | Q | IR(KBr, cm⁻¹) | NMR(DMSO-$d_6$, ppm) | M.P. (°C.) |
|---|---|---|---|---|
| 17 | H₃C-naphthyl | | 2.52(3H, s), 4.71(2H, s), 7.29~8.03(5H, m), 8.58~8.69(1H, m) | 232.7 ~ 238.2 |
| 18 | H₃CO-naphthyl | 3250, 1790, 1755, 1165 | 3.94(3H, s), 4.85(2H, s), 7.23~7.51(2H, m), 7.87~8.17(3H, m), 8.67(1H, s) | 236.4 (dec.) |
| 19 | F-naphthyl | | 4.82(2H, s), 7.67~8.33(6H, m) | 248.0 (dec.) |
| 20 | F-naphthyl | | 4.86(2H, s), 7.23~8.61(6H, m) | 177.1 ~ 184.7 |
| 21 | H₃CO, H₃CO-naphthyl | | 3.95(6H, s), 4.86(2H, s), 7.45~7.97(4H, m), 8.45~8.59(1H, m) | 260.7 (dec.) |
| 22 | Br, NC-naphthyl | 2230, 1760, 1350, 1170 | 4.88(2H, s), 7.88~8.55(4H, m), 8.73~9.00(1H, m), | 223.0 (dec.) |
| 23 | CN-naphthyl | 2225, 1760, 1350, 1170 | 4.88(2H, s), 7.81~8.46(4H, m), 8.64~8.92(2H, m), 12.60(1H, bs) | 131.0 ~ 135.8 |
| 24 | Cl, Cl, Cl, Cl-naphthyl | | 4.86(2H, s), 8.46~8.99(3H, m), 12.60(1H, bs) | 270.0 (dec.) |
| 25 | (H₃C)₂N-naphthyl | | 3.10(6H, s), 4.82(2H, s), 6.93~8.03(5H, m), 8.47(1H, s) | 256.4 (dec.) |
| 28 | NO₂-naphthyl | 1793, 1764, 1527, 1345, 1172 | 4.85(2H, s), 7.80~9.24(6H, m), 12.67(1H, bs) | 229.6 (dec.) |

TABLE 7-continued

Q-SO$_2$-N-CH$_2$-C(=O)-NH-C(=S)-

| Ex. No. | Q | IR(KBr, cm$^{-1}$) | NMR(DMSO-d$_6$, ppm) | M.P. (°C.) |
|---|---|---|---|---|
| 29 | 5-fluorobenzo[b]thiophen-2-yl | 1757, 1391, 1253, 1176 | 4.74(2H, s), 7.41~8.50(4H, m), 12.76(1H, bs) | 240.4 ~ 242.5 |
| 30 | 5-chlorobenzo[b]thiophen-2-yl | 1761, 1468, 1385, 1249, 1170 | 4.73(2H, s), 7.50~8.46(4H, m), 12.77(1H, bs) | 208.3 (dec.) |
| 31 | 3-chlorobenzo[b]thiophen-2-yl | 1784, 1756, 1462, 1374, 1245, 1173 | 4.92(2H, s), 7.50~8.34(4H, m), 12.95(1H, bs) | 275.3 (dec.) |
| 32 | 4-chlorobenzo[b]thiophen-2-yl | 1746, 1467, 1382, 1257, 1171 | 4.79(2H, s), 7.53~8.40(4H, m), 12.76(1H, bs) | 221.2 ~ 224.6 |
| 33 | 5-bromobenzofuran-2-yl | 1751, 1436, 1392, 1237, 1165 | 4.74(2H, s), 7.65~8.10(4H, m), 12.72(1H, bs) | 186.7 ~ 187.7 |
| 34 | 5-chlorobenzofuran-2-yl | 1750, 1458, 1394, 1164 | 4.74(2H, s), 7.50~8.07(4H, m), 12.83(1H, bs) | 213.9 (dec.) |
| 35 | 2-methyl-6-methylbenzothiazol-yl | 1748, 1378, 1245, 1175 | 2.88(3H, s), 4.83(2H, s), 8.13(2H, s), 8.87(1H, s), 12.62(1H, bs) | 240.4 (dec.) |
| 36 | benzimidazol-2-yl | 1785, 1758, 1449, 1388, 1255, 1185, 1160 | 4.84(2H, s), 7.26~7.86(4H, m), 12.94(1H, bs) | |
| 37 | benzo[b]thiophen-3-yl | 3111, 1793, 1762, 1463, 1374, 1174 | 4.87(2H, s), 7.47~7.68(2H, m), 8.04~8.28(2H, m), 9.01(1H, s), 1264(1H, bs) | |
| 38 | benzisothiazol-3-yl | 1757, 1386, 1167 | 4.83(2H, s), 7.50~8.34(4H, m), 12.77(1H, bs) | 203.1 (dec.) |

TABLE 7-continued

Q-SO$_2$-N(C(=S))-CH$_2$-C(=O)-NH (structure shown)

| Ex. No. | Q | IR(KBr, cm$^{-1}$) | NMR(DMSO-d$_6$, ppm) | M.P. (°C.) |
|---|---|---|---|---|
| 39 | 5-methyl-7-methoxy-benzofuran-2-yl-COCH$_3$ | 1764, 1680, 1475, 1361, 1319, 1162 | 2.59(3H, s), 4.08(3H, s), 4.77(2H, s), 7.50~8.28(3H, m), 12.51(1H, bs) | 244.0 (dec.) |
| 40 | 4-methyl-7-methoxy-benzofuran-2-yl-COCH$_3$ | 1746, 1671, 1362, 1305, 1186, 1167 | 2.63(3H, s), 4.10(3H, s), 4.85(2H, s), 7.32(1H, d, J=8.9Hz), 7.95(1H, s), 8.14(1H, d, J=8.9Hz), 12.54(1H, bs) | |
| 41 | dimethyl-coumarin-yl | 1745, 1467, 1385, 1360, 1170 | 4.81(2H, s), 6.65(1H, d, J=9.6Hz), 7.62(1H, d, J=8.9Hz), 8.04~8.58(3H, m), 12.66(1H, bs) | 230.2 (dec.) |
| 42 | 2,5-dimethyl-benzothiazol-yl | 1762, 1613, 1370, 1241, 1174 | 2.87(3H, s), 4.85(2H, s), 7.92~8.64(3H, m), 12.61(1H, bs) | 226.0 (dec.) |
| 43 | 6-methyl-1-acetyl-benzotriazol-yl | 1755, 1459, 1380, 1169 | 2.96(3H, s), 4.89(2H, s), 8.41(2H, s), 9.06(1H, s), 12.60(1H, bs) | 222.7 (dec.) |
| 44 | 5-methyl-benzisoxazol-yl | 1759, 1459, 1370, 1243, 1189, 1162 | 4.83(2H, s), 7.99~8.75(3H, m), 9.46(1H, s), 12.64(1H, bs) | 264.0 (dec.) |
| 45 | 4-methyl-benzothiophen-yl | 1745, 1476, 1362, 1267, 1199, 1170 | 4.90(2H, s), 7.46~8.55(5H, m), 12.63(1H, bs) | |
| 46 | 5-methyl-benzothiophen-yl | 1755, 1474, 1364, 1256, 1200, 1169 | 4.84(2H, s), 7.50~8.73(5H, m), 12.58(1H, bs) | |
| 47 | 7-methyl-benzothiophen-yl | 1743, 1459, 1390, 1346, 1172 | 4.91(2H, s), 7.55~8.31(5H, m), 12.71(1H, bs) | |
| 48 | furan-2-yl | 1753, 1431, 1381, 1191, 1166 | 4.68(2H, s), 6.72~6.86(1H, m), 7.54(1H, d, J=3.6Hz), 8.10(1H, d, J=1.8Hz), 12.75(1H, bs) | |

TABLE 7-continued

Q-SO₂-N connected to thiohydantoin ring structure

| Ex. No. | Q | IR(KBr, cm⁻¹) | NMR(DMSO-d₆, ppm) | M.P. (°C.) |
|---|---|---|---|---|
| 49 | 3-methyl-2,5-dichlorothiophene | 1795, 1758, 1452, 1432, 1374, 1177 | 4.77(2H, s), 7.65(1H, s), 12.85(1H, bs) | |
| 50 | 3-pyridyl | 1788, 1755, 1378, 1263, 1173 | 4.82(2H, s), 7.62~9.22(4H, m), 12.69(1H, bs) | 221.0 (dec.) |
| 51 | CH₃— | 1745, 1470, 1424, 1361, | 3.57(3H, s), 4.52(2H, s), | 213.4 |
| 52 | biphenylyl | 1765, 1456, 1374, 1171 | 4.34(2H,s), 7.47~8.23(9H, m), 12.65(1H, bs) | 216.0 |
| 54 | cyclohexyl (H) | 1791, 1757, 1735, 1453, 1353, 1236, 1169 | 1.24~2.23(10H, m), 3.90~4.32(1H, m), 4.50(2H, s), 12.70(1H, bs) | |
| 55 | H₃C-(CH₂)₇- | 1748, 1735, 1454, 1363, 1235, 1157 | 0.54~2.04(15H, m), 3.60~4.02(2H, m), 4.51(2H, s), 12.68(1H, bs) | |

Now, typical but non-limiting examples of formulations of the compound of this invention will be shown below.

Formulation A (Capsules)

Compound 13, 300 g of weight, 685 g of lactose and 15 g of magnesium stearate were weighed and mixed until the mixture became homogeneous. The mixture was then filled in No. 1 hard gelatin capsule at 200 mg each to obtain capsule preparation.

Formulation B (Tablets)

Compound 15, 300 g of weight, 550 g of lactose, 120 g of potato starch, 15 g of polyvinyl alcohol and 15 g of magnesium stearate were weighed. The weighed amount of compound 15, lactose and potato starch were mixed until accomplishing homogeneity. Then aqueous solution of polyvinylalcohol was added to the mixture and granulated by wet process. The granules were then dried, mixed with magnesium stearate and pressed into tablets, each weighing 200 mg.

Formulation C (Powder)

Compound 8, 200 g of weight, 790 g of lactose and 10 g of magnesium stearate were weighed and mixed until the mixture became homogeneous to obtain 20% powder preparation.

Formulation D (Capsules)

Compound 16, 300 g of weight, 685 g of lactose and 15 g of magnesium stearate were weighed and mixed until the mixture became homogeneous. The mixture was then filled in No. 1 hard gelatin capsule at 200 mg each to obtain capsule preparation.

Formulation E (Tablets)

Compound 19, 300 g of weight, 550 g of lactose, 120 g of potato starch, 15 g of polyvinyl alcohol and 15 g of magnesium stearate were weighed. The weighed amount of compound 15, lactose and potato starch were mixed until accomplishing homogeneity. Then aqueous solution of polyvinylalcohol was added to the mixture and granulated by wet process. The granules were then dried, mixed with magnesium stearate and pressed into tables, each weighing 200 mg.

What is claimed is:

1. A hydantoin derivative represented by formula (I):

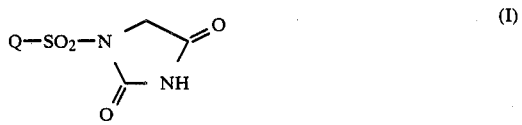

(I)

or a non-toxic salt, or a solvate, or a solvate of a non-toxic salt thereof; wherein Q represents an alkyl group having 1 or from 3 to 8 carbon atoms, a cycloalkyl group having 3 to 6 carbon atoms, a biphenylyl group, or a group:

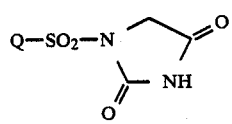

(I)

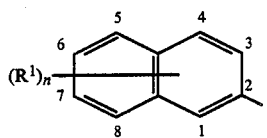

wherein R[1] represents an amino group which may be substituted with lower alkyl and/or lower alkanoyl, a halogen atom other than bromo at a position other than position 5, a lower alkyl group, an alkoxy group, a nitro group or a cyano group, or a combination of any of these groups when n represents an integer of 2 or more, and n represents an integer of 1, 2, 3 or 4.

2. A hydantoin derivative as claimed in claim 1 wherein Q represents a group:

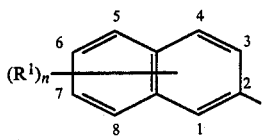

or a non-toxic salt, or a solvate or a solvate of a non-toxic salt thereof; wherein R[1] and n are as defined in claim 1.

3. A hydantoin derivative as claimed in claim 2 wherein R[1] is a halogen atom other than bromo and is located at position 1 and n represents 1.

4. A hydantoin derivative as claimed in claim 2 wherein R[1] represents a nitro group situated at position 5 and n represents 1.

5. A pharmaceutical composition for preventing or relieving diabetic complications, which comprises a pharmaceutically acceptable carrier and an effective amount of at least one hydantoin derivative represented by formula (I):

or a non-toxic salt, or a solvate, or a solvate of a non-toxic salt thereof; wherein Q represents an alkyl group having 1 or from 3 to 8 carbon atoms, a cycloalkyl group having 3 to 6 carbon atoms, a biphenylyl group, or a group:

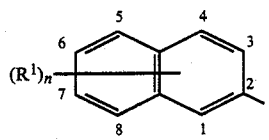

wherein R[1] represents an amino group which may be substituted with lower alkyl and/or lower alkanoyl, a halogen atom other than bromo at a position other than position 5, a lower alkyl group, an alkoxy group, a nitro group or a cyano group, or a combination of any of these groups when n represents an integer of 2 or more, and n represents an integer of 1, 2, 3 or 4.

6. A pharmaceutical composition as claimed in claim 5 wherein Q represents a group:

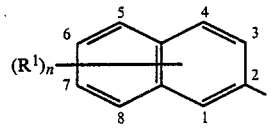

wherein R[1] and n have the same significance as defined above.

7. A pharmaceutical composition as claimed in claim 6 wherein R[1] is a halogen atom other than bromo and is located at position 1 and n represents 1.

8. A pharmaceutical composition as claimed in claim 6 wherein R[1] represents a nitro group situated at position 5 and n represents 1.

* * * * *